(12) United States Patent
Barrows

(10) Patent No.: US 11,020,275 B1
(45) Date of Patent: Jun. 1, 2021

(54) PROTECTIVE GOGGLES

(71) Applicant: Tom Barrows, Maple Grove, MN (US)

(72) Inventor: Tom Barrows, Maple Grove, MN (US)

(*) Notice: Subject to any disclaimer, the term of this patent is extended or adjusted under 35 U.S.C. 154(b) by 631 days.

(21) Appl. No.: 15/676,342

(22) Filed: Aug. 14, 2017

Related U.S. Application Data

(60) Provisional application No. 62/376,012, filed on Aug. 17, 2016.

(51) Int. Cl.
*A61F 9/02* (2006.01)
*A41D 13/12* (2006.01)

(52) U.S. Cl.
CPC ............ *A61F 9/026* (2013.01); *A61F 9/027* (2013.01)

(58) Field of Classification Search
CPC .......... A61F 9/021; A61F 9/022; A61F 9/023; A61F 9/024; A61F 9/04; A61F 9/045; A61F 9/027; A61F 9/02; A61F 17/7023; A61F 9/026; A61F 9/029; A61F 2/3854; A61F 2005/0146; A61F 9/025; A61F 17/562; A61B 17/7023; A61B 17/562; A61H 2003/0294; A46B 5/0087; A47B 2200/0088; F16H 2019/0695; A61M 16/0825; A45D 34/041; A45D 34/025; F27D 2099/0081; G02C 5/12; G02C 5/122; G02C 5/124; G02C 5/2209; G02C 5/126; G02C 5/128; G02C 5/22; G02C 5/2272; G02C 5/02; G02C 5/04; G02C 5/00; G02C 9/02; A63B 33/00; A63B 33/002; A63B 33/004; A63B 33/006; A63B 33/008; Y10T 403/32549
USPC .......................... 128/857, 858; 2/431; 351/70
See application file for complete search history.

(56) References Cited

U.S. PATENT DOCUMENTS

| | | | | |
|---|---|---|---|---|
| 2,313,282 A | * | 3/1943 | Tunke ..................... | A61F 7/103 607/109 |
| 3,336,626 A | * | 8/1967 | Schaich ............... | A45D 34/041 401/214 |
| 3,768,485 A | * | 10/1973 | Linick .................... | A61F 7/103 607/109 |
| 5,704,727 A | * | 1/1998 | Atkins .................. | F16C 11/069 403/135 |

(Continued)

FOREIGN PATENT DOCUMENTS

FR 2015FR-1562626 * 12/2015 ............. A45D 34/04

OTHER PUBLICATIONS

Higgins, "Rubber ball-and-socket mount won't slip", Jun. 1, 2000, MachineDesign, URL: https://www.machinedesign.com/archive/article/21816293/rubber-ballandsocket-mount-wont-slip (Year: 2000).*

*Primary Examiner* — Victoria J Hicks
*Assistant Examiner* — Kevin S Albers
(74) *Attorney, Agent, or Firm* — Eggink & Eggink; Anthony G. Eggink; Katrina M. Eggink

(57) ABSTRACT

A protective goggle assembly having a pair of eye cup assemblies adapted to be easily adjusted by medical personnel. A cooperating ball and socket structure is provided within a housing structure extending from each eye cup assembly and which receive the nose bridge wire ends of a formed nose bridge wire. Each socket ball has a formed channel therethrough to receive the nose bridge wire ends and to provide adjustability. The ball and socket structure permit medical personnel to rotate the nose bridge during a medical procedure without effecting the position of the eye cups covering the patient's eyes.

21 Claims, 4 Drawing Sheets

(56) References Cited

U.S. PATENT DOCUMENTS

| | | | | |
|---|---|---|---|---|
| 5,927,281 | A * | 7/1999 | Monteleone | A61F 9/0008 128/858 |
| 6,042,293 | A * | 3/2000 | Maughan | F16C 11/068 403/135 |
| 6,081,934 | A * | 7/2000 | Stefanovsky | A61F 9/022 128/858 |
| 7,188,625 | B2 | 3/2007 | Durette | |
| 7,913,326 | B1 * | 3/2011 | Barrows | A61F 9/022 2/450 |
| 9,409,056 | B2 * | 8/2016 | Lee | G02C 5/122 |
| 9,883,972 | B2 * | 2/2018 | Penninger | A61F 9/04 |
| 2005/0022823 | A1 * | 2/2005 | Davison | A61F 9/029 128/858 |
| 2006/0243286 | A1 * | 11/2006 | Durette | A61F 9/04 128/858 |
| 2007/0130674 | A1 * | 6/2007 | Beyer | A61F 9/04 2/431 |
| 2013/0090740 | A1 * | 4/2013 | Linares | A61F 2/4225 623/21.19 |
| 2015/0094157 | A1 * | 4/2015 | Lock | F16D 3/221 464/141 |
| 2018/0125709 | A1 * | 5/2018 | Schiffer | A61F 9/0026 |
| 2018/0125715 | A1 * | 5/2018 | Bellussi | A61F 9/02 |
| 2019/0000211 | A1 * | 1/2019 | Planard-Luong | A61N 1/303 |
| 2019/0167022 | A1 * | 6/2019 | Arza Moncunill | A47G 19/32 |

\* cited by examiner

PROTECTIVE GOGGLES

This application claims the benefit of U.S. Provisional Patent Application No. 62/376,012 filed on Aug. 17, 2016 and is fully incorporated by reference herein.

BACKGROUND OF THE INVENTION

The present invention relates generally to eyewear and particularly to protective eyewear worn by a patient undergoing a medical procedure. More particularly, the present invention relates to adjustable protective goggles for patients undergoing medical procedures involving the use of laser equipment.

Although various prior art protective eyewear structures have been proposed and utilized in the past for purposes of protecting the eyes of a patient during laser related medical procedures, they have all suffered from shortcomings and limitations. For example, U.S. Pat. No. 7,913,326 ('326 Patent) issued to Applicant on Mar. 29, 2011 and entitled Patient Laser Goggles describes the limitations of prior art eyewear structures requiring the adjustability of the nose bridge by medical personnel during laser related medical procedures. The protective goggles of the present invention overcome the shortcomings and limitations of the prior art by providing goggles which protect the eyes of a patient from laser exposure during a medical procedure.

The protective goggles of the present invention provide a patient goggle assembly that is easily adjusted, comfortable when worn and that provides an improvement over the patient laser goggles disclosed in the '326 Patent. The protective goggles provide a pair of eye cups adjustable with respect to a movable nose bridge to allow a medical practitioner to adjust the nose bridge without effecting the position of the eye cups that cover the patient's eyes.

SUMMARY OF THE INVENTION

A protective goggle assembly having a pair of oval shaped eye cups, each having a housing structure extending outwardly therefrom. Each housing structure has an interior with a formed socket cavity positioned adjacent an opening in the housing structure. The socket cavity may include a formed insert positioned from the inside of the eye cup to form the socket cavity and in which a socket ball is positioned. The socket ball has a formed channel extending therethrough in alignment with the opening in the housing structure so as to receive the ends of a formed nose bridge wire. The socket ball is preferably formed of an elastomeric composition, such as a rubber, so that the nose bridge may be frictionally held therein.

The formed channel in each socket ball permits the eye cups to be attached to the nose bridge and adjusted for covering the eyes of a patient in the x, y, z axis. Further the socket ball has a configuration with exterior ridges which cooperate with channels formed in the socket cavity of the housing structure interior to permit medical personnel to rotate the socket ball/nose bridge wire with respect to the eye cups during a medical procedure.

The eye cups of the protective goggle assembly may be coated with a silicone layer on the interior and around the eye cup periphery to provide patient comfort.

An advantage of the protective goggle assembly of the invention is to provide a comfortable protective eyewear structure for the patient and which provides an easily adjustable eye cup assembly for medical personnel before and during a medical procedure involving the use of laser equipment.

These advantages and other benefits of this invention will become clear from the following description by reference to the drawings.

DESCRIPTION OF THE PREFERRED EMBODIMENTS

Figure 4:
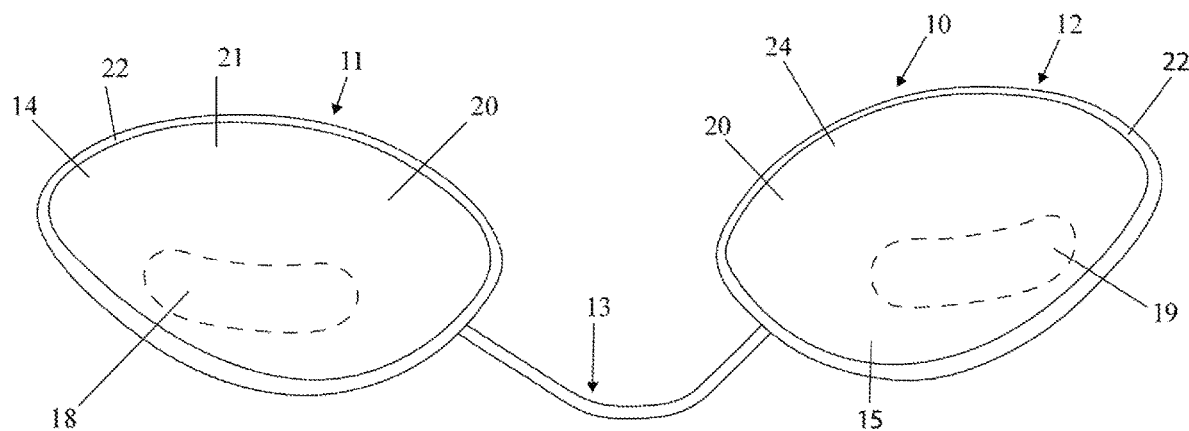
FIG. 4 is a bottom perspective view showing the protective goggles of FIG. 1.

Referring to FIGS. 1-4 the protective goggles 10 of the invention are shown to have a pair of eye cup assemblies 11 and 12 held on the generally aligned or coplanar end portions 38, 39 of formed wire nose bridge 13. The eyecup assemblies 11 and 12 are adjustably and frictionally held on the wire nose bridge end portions 38, 39, as further discussed below. Each eye cup assembly 11, 12 is shown to have an oval body configuration 14, 15, respectively, and having exterior housing structures 16, 17 extending outwardly from their respective outside surfaces. As shown in FIG. 4, formed inserts 18 and 19 are disposed in the interiors 21, 24 of the eye cup assemblies 11 and 12 in alignment with the outwardly extending housing structures 16, 17. The eye cup assemblies 11 and 12 are further shown to have a polymeric covering 20, i.e. a silicone coating which extends about the periphery 22 of each oval body 14, 15.

Figure 1:
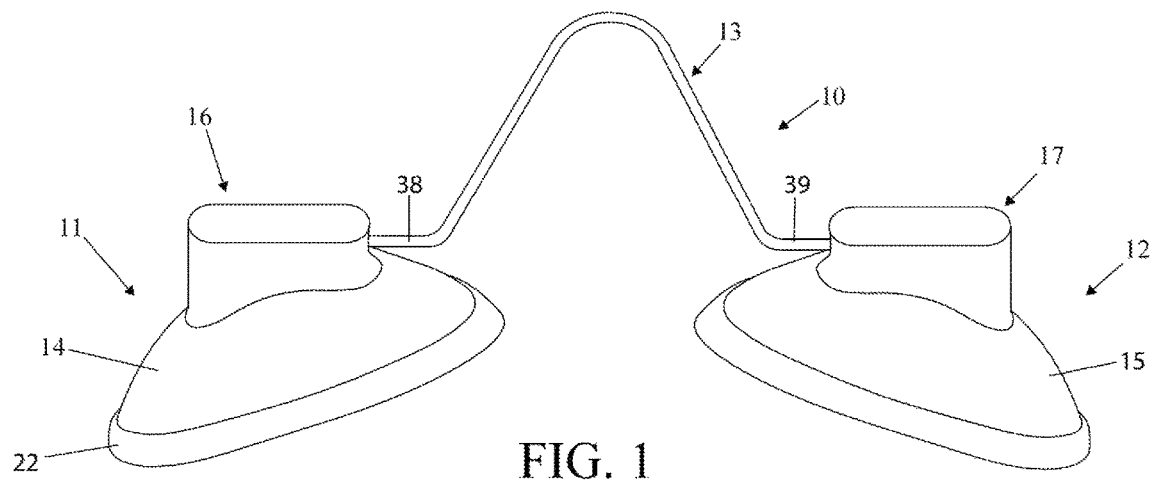
FIG. 1 is a lateral perspective view showing the protective goggles of the invention.
Figure 2:
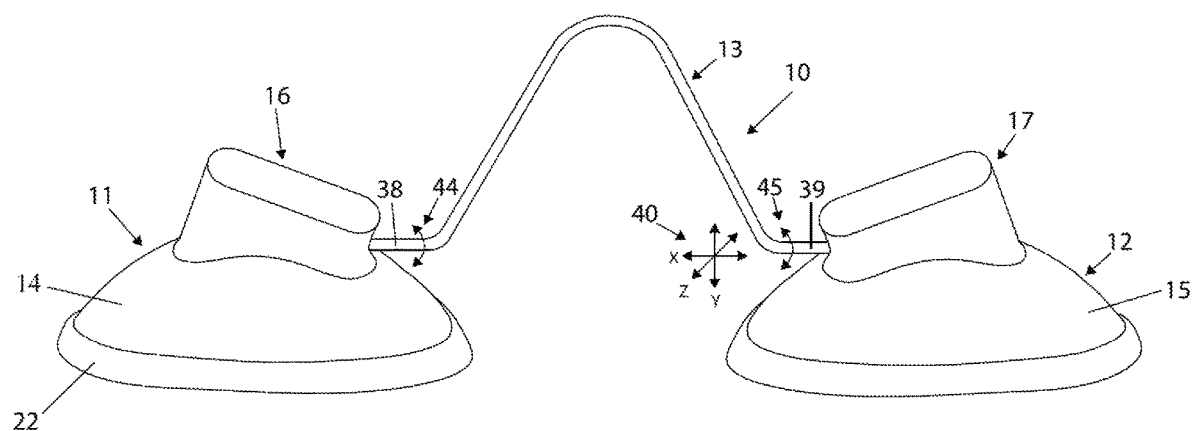
FIG. 2 is another lateral perspective view thereof.
Figure 3:
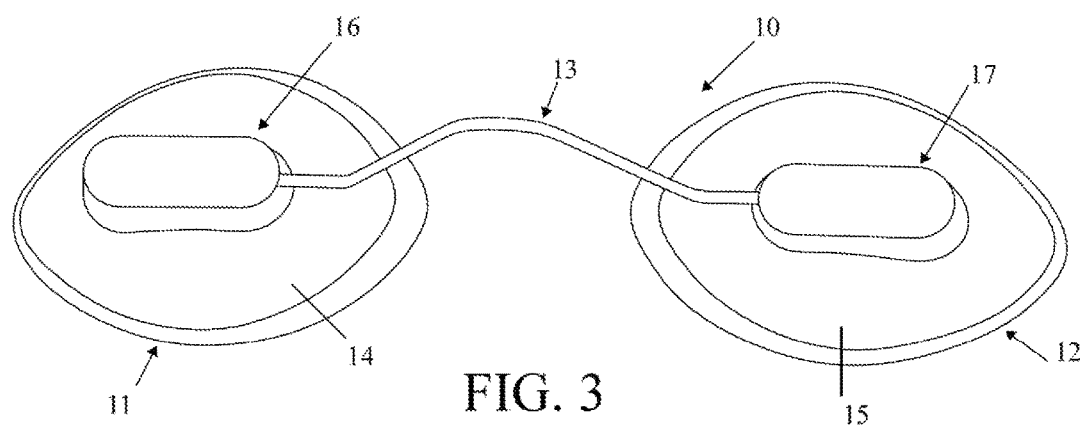
FIG. 3 is a top perspective view of the protective goggles of FIG. 1.

As shown in FIG. 2, the nose bridge 13 is able to be adjusted with respect to the eye cup assemblies 11, 12 in the x, y, z directions as depicted by axis 40. Additionally, the end portions 38, 39 of the nose bridge 13 are rotationally adjustable with respect to eye cup assemblies 11, 12 as depicted by arrows 44, 45 by means of two factors as further described below. The ability to provide adjustability of the eye cup assemblies 11, 12 and the nose bridge 13 is the result of the novel cooperation of elements contained within the housing structures 16, 17.

Figure 5:
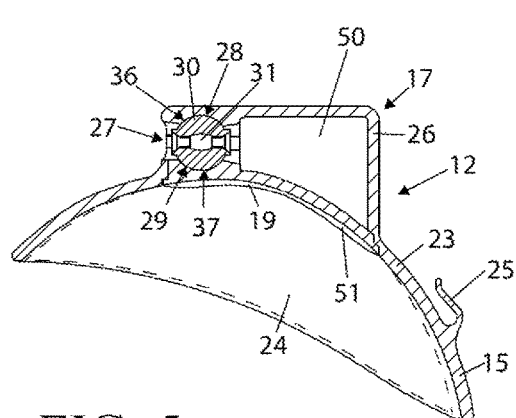
FIG. 5 is a sectional view showing an eye cup assembly of the protective goggles of FIG. 1.
Figure 7:
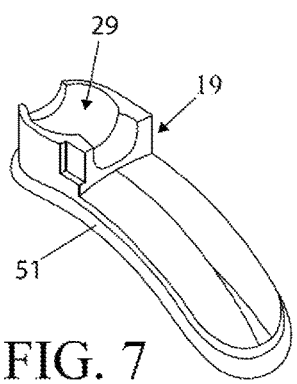
FIG. 7 is a perspective view showing the formed insert.

Referring to FIG. 5, a sectional view of eye cup assembly 12 is shown. The exterior housing 17 is shown having a formed housing structure 26 having a lateral opening or aperture 27 adjacent to which socket 29 and socket ball 30 are positioned. The socket ball 30 is shown to have a formed channel 31 extending therethrough to thereby permit the terminal or end portion 39 of the nose bridge 13 to protrude through aperture 27, through channel 31 and into the interior 50 of housing 17 and to frictionally engage the nose bridge ends which extend into interior 50. The socket ball 30, preferably formed of a rubber composition, is further shown to be held within a socket cavity which is formed by the opposing generally hemispherical cavities 28, 29 within housing structure 26 and the formed insert 19, respectively, as further shown in FIG. 7, which shows the formed insert 19. The insert 19 is shown having an elongated, curved body portion 51 which aligns within the oval body 15 of eye cup assembly 12 to form the bottom of housing 17.

Figure 6:
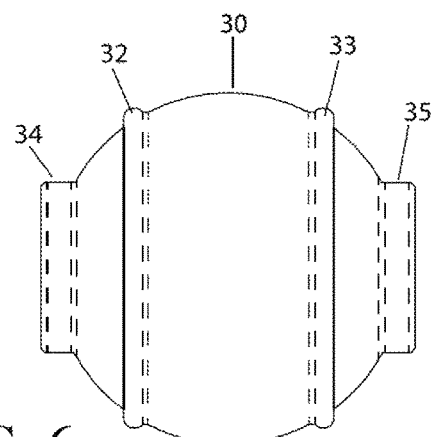
FIG. 6 is a plan view showing the socket ball of the adjustment mechanism.

Referring further to FIG. 6, the socket ball 30 is shown to have end extensions 34 and 35, through which the formed channel 31 extends. Circumferential ridges 32 and 33 are shown extending generally perpendicular to the interior channel/end extensions of the socket ball 30 and which mate with peripheral channels 36 and 37 in the socket cavity and with the end extensions 34 and 35 allow the socket ball 30 to rotate within the socket cavity.

Figure 8:
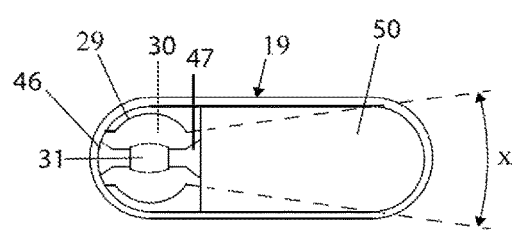
FIG. 8 is plan top view of the formed insert of FIG. 7.

FIG. 8 is a top view of the formed insert 19 forming the housing assembly and showing the angle range "x" in which the wire bridge end may be adjusted therein. The socket ball 30 and formed channel 31 are shown superimposed in socket cavity 29. The end portion 39 of the nose bridge 13 as shown in FIG. 2 may be adjusted in the x, y, z directions. The socket ball 30 is preferably formed of an elastomeric composition, such as a rubber composition, and which may rotate within the socket cavity formed by the housing interior and the formed insert 19. The formed channel 31 in FIG. 8 is shown to have flared ends 46 and 47. The diameter of the nose bridge end and the dimensions of the formed channel 31 permit the end portion 39 of the nose bridge to be adjusted within the interior 50 of the exterior housing 17. The bottom for the opening of the exterior housing 17 is provided by formed insert 19 as depicted in FIGS. 5 and 8. The angle range "x" depicts the adjustment limit within the interior 50 of the housing structure 17 and which generally conforms to the x, y, z movement permitted within the formed channel 31 of the socket ball 30, particularly as defined by the flared ends 46 and 47. The latter limitation providing for the integrity of the rubber composition of socket ball 30 which frictionally hold the respective generally coplanar nose bridge ends 38 and 39 and allows for the rotation of the socket ball 30, as indicated by arrows 44 and 45 in FIG. 2, within the respective socket cavity of eye cups 12 and 13 to thereby allow for the adjustment of the nose bridge wire when the goggle assembly is worn by a patient during a medical procedure.

Figure 9:
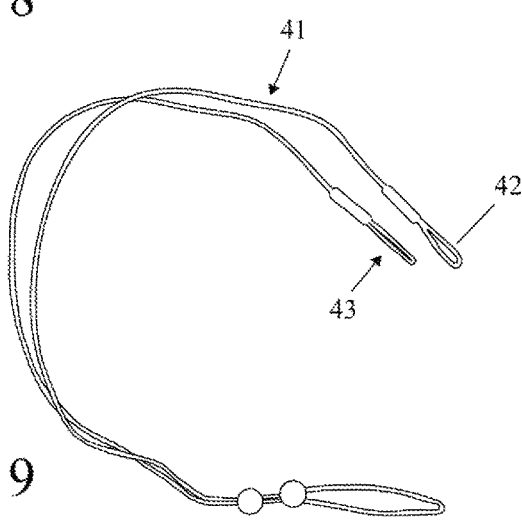
FIG. 9 is a perspective view showing the adjustable strap used in the protective goggles of the invention.

FIG. 9 is a perspective view showing the adjustable strap assembly 41 having strap loops 42 and 43 which attach to hook 25 of the respective eye cup assemblies as shown in Figure S with respect to eye cup assembly 12. As shown, the strap assembly 41 has slidable members which permit the loops 42 and 43 to be adjusted and slidable members which permit the strap to be adjusted around the patient's head to thereby maintain the position of the eye cup assemblies to cover the eyes of a patient.

Figure 10:
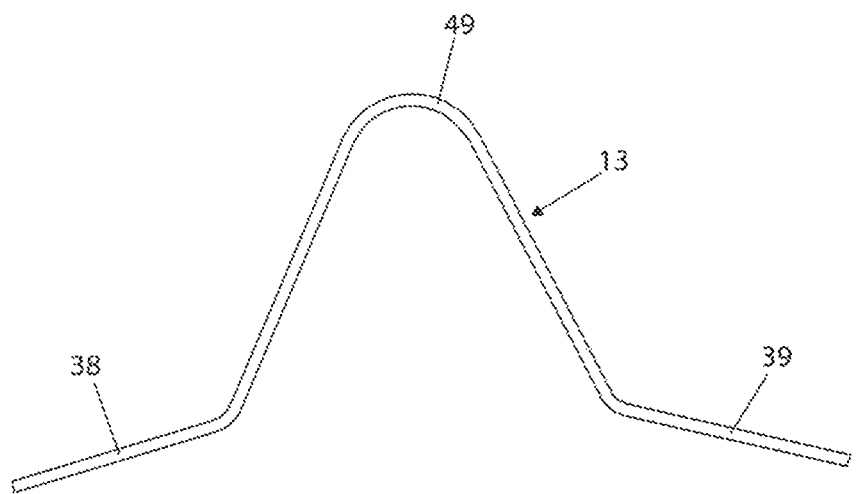
FIG. 10 is an enlarged view of the nose bridge wire structure of the invention.

The nose bridge wire structure 13 is shown in FIG. 10 having the upwardly formed midbend 49 which may be rotated over the nose of a patient during a medical procedure. The nose bridge 13 is further shown to have end portions 38 and 39 which are placed within the housing structures 16 and 17 of the eye cup assemblies 11 and 12, respectively. The end portions 38 and 39 are shown to have a generally coplanar relationship and on which the respective eye cup assemblies may be adjusted to cover the eyes of a patient as further described with respect to FIGS. 1-4.

Figure 11:
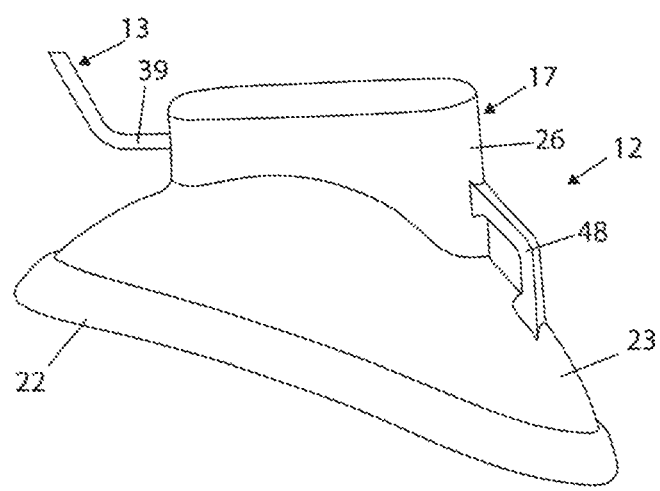
FIG. 11 is a lateral perspective view showing an attachment loop incorporated onto the eye cup assembly of the invention.

FIG. 11 shows eye cup assembly 12 having an alternate means for engaging a strap to hold the protective goggles 10 on the face of a patient. For example, as opposed to utilizing a hook structure 25 as shown in FIG. 5 for use with strap assembly 41 of FIG. 9, an attachment loop 48 may be formed extending from the housing structure 26 to the exterior surface 23 of the eye cup assembly 12 to provide an attachment structure for use with an adjustable strap assembly. The attachment 48 may be of any shape and be unitary with the formed structure of the eye cup assembly 12, i.e., a metallic or polymeric molded or formed eye cup structure compatible for protective use during a medical procedure involving laser equipment.

As many changes are possible to the protective goggle embodiments of this invention utilizing the teachings thereof, the descriptions above, and the accompanying drawing should be interpreted in the illustrative and not in the limited sense.

That which is claimed is:

1. An adjustable protective goggle assembly comprising:
   a) a pair of oval shaped eye cup assemblies, each having an oval body, an inside surface, an outside surface and a periphery,
   b) an elongated housing structure extending outward from said outside surface of said oval body of each said eye cup assembly, said elongated housing structure having an interior, a lateral aperture and a formed spherical socket cavity adjacent said lateral aperture, said spherical socket cavity having a continuous peripheral channel generally spatially perpendicular said lateral aperture,
   c) a spherical socket ball having a formed channel extending therethrough and having a continuous circumferential ridge extending outwardly therefrom, said socket ball being mounted for rotation within said formed socket cavity and said continuous channel of said spherical socket cavity of said elongated housing structure, said formed channel through said socket ball having flared ends and being aligned with said lateral aperture of said housing structure;
   d) each said oval eye cup assembly having a bottom opening aligned with said elongated housing structure and having a formed insert extending upward into said bottom opening of said housing structure, said formed insert having a generally hemispherical depression therein and said housing structure having a generally hemispherical interior which form said spherical socket cavity for containing said spherical socket ball; and
   e) a formed nose bridge wire having a midbend and terminal ends, said terminal ends for insertion through each said lateral aperture of said housing structure and into said formed channel of said spherical socket ball, said terminal ends of said formed nose bridge wire being contained in said interior of said housing structure, whereby said formed channel through said spherical socket ball allows said terminal ends of said formed nose bridge wire to be adjusted with respect to said pair of eye cup assemblies in the x, y, and z directions and to be frictionally held therein and rotated therewith subsequent adjustment.

2. The protective goggle assembly of claim 1, wherein said inside surface and said periphery of each said oval shaped eye cup assemblies have a polymeric coating.

3. The protective goggle assembly of claim 1, wherein said eye cup assemblies are formed of a metal or plastic composition and wherein said socket ball is formed of an elastomeric composition.

4. The protective goggle assembly of claim 1, wherein said socket ball has opposing end portions extending therefrom.

5. The protective goggle assembly of claim 1, wherein said formed channel of said spherical socket ball has a first diameter and wherein said formed bridge wire has a second diameter and wherein said first diameter is greater than said second diameter.

6. The protective goggle assembly of claim 1, wherein each of said oval shaped eye cup assemblies has a hook or loop structure mounted on said outside surface for receiving an adjustable strap assembly.

7. The protective goggle assembly of claim 6, wherein said oval shaped eye cup assembly, said housing structure and said hook or loop structure form a unitary structure and wherein said formed insert is held within said eye cup assembly by means of a weld.

8. The protective goggle assembly of claim 1, wherein said spherical socket cavity has a second continuous peripheral channel and wherein said spherical socket ball has a second continuous peripheral ridge extending circumferentially outwardly therefrom for rotation in said second continuous peripheral channel of said spherical socket cavity.

9. The protective goggle assembly of claim 4, wherein said housing cavity has cylindrical depressions and wherein said opposing ends of said spherical socket ball are positioned for rotation within said cylindrical depressions in said housing cavity.

10. An eye cup assembly comprising an oval shaped cup structure having an inside surface, an outside surface and a periphery, said outside surface having an elongated housing structure extending outward therefrom, said elongated housing structure having an interior, a lateral aperture and a socket cavity adjacent said lateral aperture, said socket cavity having a continuous circumferential channel spatially parallel said lateral aperture, a socket ball having a continuous circumferential ridge extending outwardly therefrom for matingly engaging said continuous circumferential channel of said socket cavity and mounted for rotation in said socket cavity, said socket ball further having a formed channel therethrough, said formed channel being constructed and arranged to receive the terminal end of a formed nose bridge having a midbend spatially distant from the terminal end, whereby said formed channel within said socket ball allows the terminal end of the formed nose bridge to be adjusted in the x, y, and z directions and frictionally held and rotated with said socket ball and whereby the terminal end of the formed nose bridge is contained in said interior of said housing structure.

11. The eye cup assembly of claim 10, wherein said socket ball is constructed of rubber.

12. The eye cup assembly of claim 10, wherein said formed channel of said socket ball has flared ends.

13. The eyecup assembly of claim 10, wherein said housing structure is unitary with said oval shaped eye cup structure.

14. The eye cup assembly of claim 10, wherein said cup structure is constructed of metal or plastic composition.

15. The eye cup assembly of claim 10, wherein said socket ball and said continuous circumferential channel are partially contained in an insert which is welded to the interior of said oval shaped cup structure.

16. The eye cup assembly of claim 10, wherein a book or loop attachment structure for a strap assembly is mounted on said outside surface of said eye cup.

17. The eye cup assembly of claim 10, wherein said eye cup structure has a peripheral circumferential ridge and wherein said peripheral circumferential ridge and said interior surface of said cup structure are coated with silicone.

18. An adjustable protective goggle assembly comprising
a) a pair of oval shaped eye cup assemblies, each having an oval cupped body, an inside surface and an outside surface;
b) an elongated housing structure extending from said outside surface of each said oval cupped body, said elongated housing structure forming an enclosure and having a lateral aperture and a socket cavity therein adjacent said lateral aperture, said socket cavity having a continuous peripheral channel generally spatially perpendicular said lateral aperture;
c) a socket ball mounted within said socket cavity, said socket ball formed of an elastomeric material and having a continuous peripheral ridge extending circumferentially outwardly therefrom for rotation in said continuous peripheral channel of said socket cavity, a formed channel extending through said socket ball, said formed channel having opposing flared ends and being aligned with said lateral aperture of said housing structure to thereby receive and frictionally hold terminal ends of a formed nose bridge wire; and
d) said rigid formed nose bridge wire having opposing said terminal ends and a middle bend spatially outward said opposing terminal ends, whereby said terminal ends of said nose bridge wire can be adjusted in the x, y, and z planes with respect to said eye cup assemblies and rotated with said socket ball and wherein said terminal ends of said formed nose bridge wire are contained in said housing enclosure subsequent adjustment, and whereby subsequent adjustment said rigid formed bridge wire may be rotated with said socket ball with respect to the face of a wearer.

19. The protective goggle assembly of claim 18, wherein a formed insert extends upward into said housing structure from said inside surface of each said oval cupped body, said formed insert having a generally hemispherical depression therein to form said socket cavity for receiving said socket ball, and said housing structure having a generally hemispherical interior which in cooperation with said hemispherical depression of said formed insert forms said socket cavity for containing said socket ball.

20. The protective goggle assembly of claim 18, wherein said socket cavity has a second continuous peripheral channel and wherein said socket ball has a second continuous peripheral ridge extending circumferentially outwardly therefrom for rotation in said second continuous peripheral channel of said socket cavity.

21. The protective goggle assembly of claim 18, wherein said eye cup assemblies are formed of a metal or plastic composition and wherein said elastomeric material of said socket ball is a rubber composition.

* * * * *